United States Patent [19]

Walliczek

[11] 4,136,172

[45] Jan. 23, 1979

[54] FUNGICIDAL COMPOSITION AND METHOD OF USE

[75] Inventor: Erwin G. Walliczek, Beaumaris, Australia

[73] Assignee: ICI Australia Limited, Melbourne, Australia

[21] Appl. No.: 661,021

[22] Filed: Feb. 24, 1976

[30] Foreign Application Priority Data

Mar. 10, 1975 [AU] Australia ............................. PC0850

[51] Int. Cl.$^2$ ............................................ A61K 33/34
[52] U.S. Cl. ................................................... 424/141
[58] Field of Search ................ 424/141, 143, 342, 341

[56] References Cited

U.S. PATENT DOCUMENTS 2,558,762    7/1951    Kohr ..................................... 424/141

FOREIGN PATENT DOCUMENTS 45-40915  12/1970  Japan ......................................... 424/141
  967514    8/1964  United Kingdom ..................... 424/141

OTHER PUBLICATIONS

Soine et al., Rogers' Inorganic Pharm. Chem., Lea & Febiger, Phila. (1961), pp. 331–332.

*Primary Examiner*—Frederick E. Waddell
*Attorney, Agent, or Firm*—Cushman, Darby & Cushman

[57] ABSTRACT

A pharmaceutical composition comprising a solution of copper ions in a polyether containing from 2 to 200 inclusive ether groups.

19 Claims, No Drawings

FUNGICIDAL COMPOSITION AND METHOD OF USE

This invention relates to pharmaceutical compositions for the control of certain diseases in animals and human beings. Mycotic dermatoses in animals, for example local and generalised ring worm, mycotic otitis externa, plantar warts (papillomas), tinea, woods lamp, whitlow (paronychia), etc. are difficult to control using known fungicidal compositions.

We have now found a composition which is effective in the control and eradication of a large number of fungal diseases.

Accordingly we provide a pharmaceutical composition comprising a solution of copper ions in a polyether containing from 2 to 200 inclusive ether groups. The copper ions in the pharmaceutical compositions of our invention are in association with pharmaceutically acceptable anions such as halide, sulphite, phosphate or organic anions, the association being either in the form of a simple salt or in the form of an anionic complex.

Where the copper ions are in the form of an anionic complex the anionic complex ions are associated with equivalent concentrations of cations. The nature of the associated cations is not critical as long as they are pharmaceutically acceptable and suitable cations are for example the ions of hydrogen, of alkali metals, of alkaline earth metals and ammonium ions. In addition such anionic complexes may optionally contain a pharmaceutically acceptable nonionic ligand such as sulphur dioxide or nonionic organic compounds.

The polyether in the pharmaceutical compositions of our invention may be for example a condensate of ethylene oxide, propylene oxide, butylene oxide or mixtures thereof; a sequential or random cocondensate of ethylene oxide, propylene oxide and/or butylene oxide; or a condensate of aliphatic alcohols containing from 1 to 24 carbon atoms, alkylphenols or fatty acids with ethylene oxide or propylene oxide optionally cocondensed either sequentially or randomly with higher alkylene oxides such as propylene oxide or butylene oxide; provided that said polyether is pharmaceutically acceptable. Optionally the polyether may be substituted with phosphate, sulphate, ester or carboxy groups provided that said substituted polyether is pharmaceutically acceptable.

Preferred polyethers are polyoxyalkylene condensates comprising aliphatic alcohols containing from 1 to 24 carbon atoms, alkyl phenols and fatty acids, condensed with 2 to 20 moles of ethylene oxide or propylene oxide optionally cocondensed either sequentially or randomly with 2 to 20 moles of higher alkylene oxides such as propylene oxide or butylene oxide; provided said polyethers are pharmaceutically acceptable.

Typical examples of preferred polyethers are pharmaceutically acceptable polyethers chosen from the group consisting of methanol condensed with 2 moles of ethylene oxide; ethanol condensed with 2 or 3 moles of ethylene oxide; butanol condensed with 2 to 4 moles of ethylene oxide; methanol condensed sequentially or randomly with 2–6 moles of ethylene oxide and/or 2 to 6 moles of propylene oxide; $C_4$–$C_{10}$ saturated, branched or linear, aliphatic alcohols condensed with 2–10 moles of ethylene oxide and optionally, sequentially or randomly condensed with 2–10 moles of propylene oxide or butylene oxide; $C_{10}$–$C_{20}$ branched or linear, alcohols condensed with 4–20 moles of ethylene oxide and optionally sequentially or randomly condensed with 2–20 moles of propylene oxide or butylene oxide; $C_4$–$C_{20}$ alkyl phenols, $C_8$–$C_{20}$ fatty acids, $C_8$–$C_{20}$ fatty amides, $C_8$–$C_{20}$ fatty amines, or diphenylol propane, each condensed with 4–20 moles of ethylene oxide and optionally, either sequentially or by random addition, condensed with 4–20 moles of propylene oxide or butylene oxide; polypropylene glycol of molecular weight 900–4000 condensed with 10 to 90% of the total molecule by weight with ethylene oxide; and derivatives thereof prepared for example by esterification with inorganic or organic acids.

The most preferred polyethers are pharmaceutically acceptable condensates, or random or sequential cocondensates, of 1 mole of a lower aliphatic alcohol such as methanol, ethanol, n-propanol and isopropanol with 4 to 12 moles of one or more of the alkylene oxides chosen from the group consisting of ethylene oxide, propylene oxide and butylene oxide.

The nature of the copper ion containing moiety in our pharmaceutical compositions is not fully understood, but it is believed that copperions in the cuprous state and anions are associated in the form of anionic complex ions which are solvated by the polyether.

The proportion of copper in the pharmaceutical compositions of our invention is in the range from 0.01 to 12 percent by weight and is preferably from 0.01 to 7 percent by weight. The proportion of the polyether is in the range from 5 to 99.95 percent by weight and is preferably from 50 to 99.9 percent by weight.

The pharmaceutical compositions of our invention comprising copper ions associated with anions and polyether, as hereinbefore defined, may be made by extracting an aqueous solution of a copper salt, and optionally a chosen alkali metal or alkaline earth metal salt, with the chosen polyether. For example a pharmaceutical composition of our invention may be prepared by extracting an aqueous solution of cuprous chloride and sodium chloride with a polyether such as the condensate of 4 moles of ethylene oxide and 2 moles of propylene oxide with 1 mole of methanol. Such a composition may also be obtained by dissolving a mixture of the appropriate amounts of cuprous chloride, sodium chloride and water in the chosen polyether.

An alternative process for the preparation of the pharmaceutical compositions of our invention comprises, for example, the exposure of a mixture of cupric chloride dihydrate and a polyether, as hereinbefore defined, to visible or ultraviolet light in the absence of air or oxygen.

The most preferred pharmaceutical compositions of our invention comprise cuprous ions in association with chloride ions and a polyether as hereinbefore defined.

In the pharmaceutical compositions of our invention it is preferable to maintain the copper in the cuprous state. This may be done by preventing air from contacting the compositions or if oxidation has occurred, which is usually evidenced by change in appearance of the solution from colourless to progressively darker shades of yellow and brown, simply by exposing the solution in a clear glass, stoppered container, to sunlight. If preferred, oxidation of the cuprous copper in the compositions may be prevented by the addition of a pharmaceutically acceptable reducing agent. Suitable reducing agents are sulphur dioxide, sodium metabisulphite, ammonium bisulphite and the like. The reducing agent expressed as equivalent sulphur dioxide can be in the range of 0.05 to 15 percent by weight and is typically from 0.05 to 1.0 percent by weight. The polyether will act as a reducing agent in the presence of sunlight.

The pH of the pharmaceutical compositions of our invention may be varied within wide limits according to the type of application but the compositions are most stable at a pH in the range from 1 to 7. For the application of the pharmaceutical compositions of our invention to human beings we have found that a pH in the range from 1 to 7 and preferably from 2 to 5 is satisfactory and that lower or higher pH's tend to cause discomfort to the patient.

As indicated hereinbefore the pharmaceutical compositions of our invention can be applied topically. They may be further formulated into gels, creams, pastes, lotions and solutions for topical application.

A pharmaceutical composition of our invention may be in the form of a solution, a gel, an ointment, a paste or an emulsion such as a cream or lotion. Each of these types of formulation may be obtained using conventional procedures known to those skilled in the art and by using known excipients.

A solution may be obtained by diluting a composition of our invention with pharmaceutically acceptable liquids, for example ethanol, n-propanol, isopropanol, propylene glycol, glycerol and polyethers. These diluents clearly may only be incorporated in such a pharmaceutical composition to an extent which causes no precipitation or phase separation, and this can be readily determined by experiment.

A gel may be obtained by adding a gelling agent to a composition of our invention as defined hereinabove, and examples of suitable gelling agents are carboxypolymethylene, polyvinylpyrrolidone, polyvinyl acetate, cellulose derivatives such as methyl-, ethyl-, hydroxyethyl-, hydroxypropylmethyl- or sodium carboxymethyl- cellulose, alginates, bentonites and silica.

An ointment may be obtained by dispersing a composition of our invention as defined hereinabove in an essentially immiscible organic phase, for example soft paraffin, optionally in the presence of an emulsifying and/or thickening agent, for example sorbitin monostearate.

A paste may be obtained by thickening a composition of our invention as defined hereinabove with a solid material such as magnesium stearate, zinc oxide, a silicate or starch.

Emulsions such as creams or lotions may be obtained by mixing a composition of our invention as defined hereinabove with a suitable emulsifying system.

The compositions may also contain other pharmaceutically active ingredients, for example antibacterial agents, other antifungal agents, keratolytic agents or anti-inflammatory antipyretic or vascodilatory agents, as well as conventional excipients such as colours or preservatives as desired.

The compositions should contain from 0.01 to 12 percent by weight of copper and preferably 0.05 to 5 percent by weight.

The compositions are applied topically to the area to be treated or the area of infection and may be applied as a gel, cream, lotion, paste, ointment or solution. The solutions may be painted onto the skin or applied as a spray or aerosol.

The compositions may be applied directly to the skin or else impregnated into a suitable carrier and applied to the skin in a bandage.

The pharmaceutical compositions or our invention have been successful in the eradication of otitis externa, commonly known as ear canker, in dogs by topical application. Long-eared breeds such as cocker spaniels are known to be subject to chronic otitis externa and success in the eradication of this condition has followed from topical application of the compositions. It would appear that the compositions not only control the infective agent but also rapidly reduce the dermal hypertrophy commonly associated with such conditions.

Topical application of the pharmaceutical compositions of our invention has been successful in the cure of fungal diseases such as ring worm, tinea, plantar warts, whitlow, woods lamp and etc. in man.

When topically applied, the pharmaceutical compositions of our invention have shown success in the relief of the symptoms and pain of arthritis in man.

The invention is now illustrated by, but by no means limited to, the following examples.

EXAMPLE 1

To one liter of a saturated sodium chloride solution was added 100 g of purified cuprous chloride powder. To prevent oxidation the resulting mixture was stirred by passage of nitrogen until the cuprous chloride was completely dissolved. sufficient sulphur dioxide was added to the solution to give it a concentration of approximately 0.5 g/l of sulphur dioxide. This solution was then extracted with one liter of a polyether prepared by sequentially condensing one mole of methanol with four moles of ethylene oxide and two moles of propylene oxide. The phases were allowed to separate and the colourless polyether layer removed and stored in a well stoppered nitrogen filled container to prevent ingress of air.

EXAMPLE 2

Cuprous chloride was dissolved to the limit of its solubility in a solution saturated with both sodium chloride and sulphur dioxide at room temperature. Samples of this solution were then treated with the polyethers of Table I by the following general method, to extract the cuprous copper into the organic polyether.

A sample (20 ml) of the above saturated solution was extracted with the polyether (20 ml) at room temperature. The phases were allowed to separate and the polyether layer removed and stored in a well stoppered nitrogen filled container to prevent the ingress of air.

TABLE I

| Experiment | Polyether |
| --- | --- |
| 1. | "Ucon" 660 ("Ucon" is a registered Trade Mark for a polyalkoxylated alcohol) |
| 2. | A sequential condensate of 4 moles of ethylene oxide and 4 moles of propylene oxide with 1 mole of methanol |
| 3. | A condensate of 11 moles of ethylene oxide with 1 mole of nonylphenol |
| 4. | Polyethylene glycol of average molecular weight 1500 |
| 5. | A sequential condensate of 4 moles of ethylene oxide and 3 moles of propylene oxide with 1 mole of methanol. |
| 6. | A sequential condensate of 4 moles of ethylene oxide and 5 moles of propylene oxide with 1 mole of methanol. |

EXAMPLE 3

Cupric chloride dihydrate (13.5g) was partially dissolved in a polyether (100 ml) prepared by sequential condensation of 1 mole of methanol with 4 moles of ethylene oxide and 2 moles of propylene oxide. The resulting mixture in a stoppered clear glass bottle was placed in direct sunlight. After exposure to sunlight for about 50 hours with occasional shaking all of the cupric chloride had dissolved and the originally dark-brown solution had lightened progressively to give a colourless clear solution. Polarographic analysis showed that the copper present in the polyether solution was in the cuprous state.

Lower concentration cuprous copper compositions were prepared following a method analogous to that described above, the solution of the cupric chloride and its reduction to cuprous chloride proceeding at a faster rate.

EXAMPLE 4

A portion of the stock solution prepared in Example 1 was diluted with more of the polyether to obtain a solution containing 1% w/w copper. Six persons suffering from tinea of the feet were treated daily with the solution for 14 days. The solution was applied by brushing onto the infected area. After 14 days the symptoms of tinea had completely disappeared in all the subjects and had not reappeared after six weeks.

EXAMPLE 5

A portion of the solution prepared as described in Example 3 and containing 5% by weight cuprous copper was used to treat plantar warts (Papillomas) on the foot of a 10 year old human male. One drop of the solution was applied to each wart each day before retiring. After about 1 month's treatment all of the warts had been ejected and treatment was discontinued. One month later it was confirmed that the warts had been successfully removed, the only remaining trace of the warts being a tiny mark visible at the centre of each site.

EXAMPLE 6

A portion of the solution prepared as described in Example 1 was diluted with more polyether to obtain a solution containing 1% by weight cuprous copper. Two persons suffering from fungus infections (Woods Lamp) to the toenails were treated with the solution by brushing onto the infected areas. After one month the condition had much improved and the treatment was repeated. After a further two months the infection has been cured.

I claim:

1. A pharmaceutical composition for the treatment of topical fungal diseases in animals comprising a solution of cuprous copper ions in association with halide ions in a pharmaceutically acceptable polyether chosen from the group consisting of:
  a liquid condensate of ethylene oxide, propylene oxide, butylene oxide or mixtures thereof;
  a sequential or random cocondensate of ethylene oxide, propylene oxide, butylene oxide or mixtures thereof; or a condensate of aliphatic alcohol containing from 1 to 24 carbon atoms, an alkylphenol or a fatty acid with ethylene oxide or propylene oxide as such or cocondensed either sequentially or randomly with propylene oxide or butylene oxide;
  a liquid alcohol alkoxylate prepared by condensation of ethylene oxide, propylene oxide, butylene oxide or mixtures thereof with an aliphatic alcohol containing 1 to 24 carbon atoms; and
  a liquid phenol alkoxylate prepared by condensation of ethylene oxide, propylene oxide, butylene oxide or mixtures thereof with an alkyl phenol containing 4 to 20 carbon atoms, the proportion of copper in the solution being in the range of 0.01 to 12 percent by weight, said composition being prepared by the extraction with said polyether of an aqueous solution saturated with a halide salt of an alkali or alkaline earth metal and comprising a cuprous halide salt and optionally a mild reducing agent, or exposing a mixture comprising cupric chloride dihydrate and said polyether, in the absence of air or oxygen, to visible or ultraviolet light.

2. A composition according to claim 1 wherein said polyether is chosen from the group consisting of: methanol condensed with 2 moles of ethylene oxide; ethanol condensed with 2 or 3 moles of ethylene oxide; butanol condensed with 2 to 4 moles of ethylene oxide; methanol condensed sequentially or randomly with at least one of: 2-6 moles of ethylene oxide and 2 to 6 moles of propylene oxide: $C_4$-$C_{10}$ saturated, branched or linear, aliphatic alcohols condensed with 2-10 moles of ethylene oxide as such or sequentially or randomly condensed with 2-10 moles of propylene oxide or butylene oxide; $C_{10}$-$C_{20}$ branched or linear, alcohols condensed with 4-20 moles of ethylene oxide as such or sequentially or randomly condensed with 2-20 moles of propylene oxide or butylene oxide; $C_4$-$C_{20}$ alkyl phenols, $C_8$-$C_{20}$ fatty acids, $C_8$-$C_{20}$ fatty amides, $C_8$-$C_{20}$ fatty amines, or diphenylol propane, each condensed with 4-20 moles of ethylene oxide as such or sequentially or by random addition, condensed with 4-20 moles of propylene oxide or butylene oxide; polypropylene glycol of molecular weight 900–4000 condensed with 10 to 90% of the total molecule by weight with ethylene oxide; and esters thereof prepared by esterification with inorganic or organic acids.

3. A composition according to claim 1 wherein copper ions are in association with chloride ions, and the polyether is a pharmaceutically acceptable condensate, or random or sequential cocondensate of 1 mole of a lower aliphatic alcohol with 4 to 12 moles of one or more of the alkylene oxides chosen from the group consisting of ethylene oxide, propylene oxide and butylene oxide.

4. A composition according to claim 3 wherein the copper ions are in association with chloride ions and the polyether is a sequential condensate of 1 mole of methanol with 4 moles of ethylene oxide and 2 moles of propylene oxide.

5. A composition according to claim 1 wherein the proportion of copper in the solution is in the range of 0.01 to 7 percent by weight.

6. A composition according to claim 1 wherein the proportion of polyether in the solution is in the range from 5 to 99.95 percent by weight.

7. A composition according to claim 6 wherein the proportion of polyether in the solution is in the range from 50 to 99.9 percent by weight.

8. A composition according to claim 1 wherein the solution comprises a reducing agent expressed as equivalent sulphur dioxide in the range from 0.05 to 15 percent by weight.

9. A composition according to claim 8 wherein the solution comprises a reducing agent expressed as equivalent sulphur dioxide in the range from 0.05 to 1.0 percent by weight.

10. A composition according to claim 1 wherein the pH is in the range of 1.0 to 7.0.

11. A composition according to claim 10 wherein the pH is in the range of 2.0 to 5.0.

12. A composition according to claim 1 which is in the form of a solution, gel, paste, ointment, cream or lotion suitable for topical application to the skin of animals and human beings.

13. A composition according to claim 1 which additionally contains other pharmacologically active ingredients.

14. A method of treating fungal infections of the skin of animals and human beings which comprises topically applying to said skin an effective amount of a composition according to claim 1.

15. A method of treating fungal infections of the skin of animals and human beings which comprises topically applying to said skin an effective amount of a composition according to claim 3.

16. A method of treating fungal infections of the skin of animals and human beings which comprises topically applying to said skin an effective amount of a composition according to claim 4.

17. A process for the preparation of a composition according to claim 1 which comprises extracting an aqueous solution saturated with a halide salt of an alkali or alkaline earth metal and comprising a cuprous halide salt and optionally a mild reducing agent, with a polyether and separating the resulting colourless polyether solution.

18. A process for the preparation of a composition according to claim 3 which comprises exposing a mixture comprising cupric chloride dihydrate in a polyether, in the absence of air or oxygen, to visible or ultraviolet light.

19. A method of treating topical fungal infections of animals which comprises topically applying, to an animal in need of such treatment, an effective amount of a composition according to claim 1.

* * * * *